US010940208B2

(12) United States Patent
Morpurgo (10) Patent No.: US 10,940,208 B2
(45) Date of Patent: Mar. 9, 2021

(54) NANOASSEMBLED COMPLEXES OF NUCLEIC ACIDS, AVIDIN AND BIOTINYLATED COMPOUNDS FOR USE AS DRUG CARRIERS

(71) Applicant: LIVERA SRL, Padua (IT)

(72) Inventor: Margherita Morpurgo, Padua (IT)

(73) Assignee: UVERA SRL, Milan (IT)

( * ) Notice: Subject to any disclaimer, the term of this patent is extended or adjusted under 35 U.S.C. 154(b) by 0 days.

(21) Appl. No.: 15/743,486

(22) PCT Filed: Jul. 8, 2016

(86) PCT No.: PCT/EP2016/066240
§ 371 (c)(1),
(2) Date: Jan. 10, 2018

(87) PCT Pub. No.: WO2017/009215
PCT Pub. Date: Jan. 19, 2017

(65) Prior Publication Data
US 2018/0200376 A1    Jul. 19, 2018

(30) Foreign Application Priority Data

Jul. 10, 2015    (IT) .................... 102015000032694

(51) Int. Cl.
| | |
|---|---|
| A61K 47/62 | (2017.01) |
| A61K 47/60 | (2017.01) |
| A61K 47/54 | (2017.01) |
| A61K 31/704 | (2006.01) |
| A61K 47/65 | (2017.01) |
| A61K 47/55 | (2017.01) |
| A61K 31/573 | (2006.01) |

(52) U.S. Cl.
CPC ............ *A61K 47/62* (2017.08); *A61K 31/573* (2013.01); *A61K 31/704* (2013.01); *A61K 47/545* (2017.08); *A61K 47/549* (2017.08); *A61K 47/551* (2017.08); *A61K 47/60* (2017.08); *A61K 47/65* (2017.08)

(58) Field of Classification Search
CPC ...... A61K 47/62; A61K 47/60; A61K 31/704; A61K 47/545; A61K 31/573; A61K 47/549

USPC .......................................................... 514/34
See application file for complete search history.

(56) References Cited

U.S. PATENT DOCUMENTS

| | | | |
|---|---|---|---|
| 8,486,639 B2 * | 7/2013 | Morpurgo | A61K 31/4188 435/6.19 |
| 2003/0185793 A1 * | 10/2003 | Kratz | A61P 37/00 424/85.1 |

FOREIGN PATENT DOCUMENTS

| | | |
|---|---|---|
| WO | 2009/003951 A1 | 1/2009 |
| WO | 2015/011675 A1 | 1/2015 |

OTHER PUBLICATIONS

Yuan et al. pH-triggered blooming of 'nano-flowers' for tumor intracellular drug delivery. Chem. Commun., 2012, 48, 8129-8131. (Year: 2012).*
International Search Report and Written Opinion for corresponding Application No. PCT/EP2016/066240 (dated Sep. 26, 2016).
Hermanson, "Bioconjugate Techniques (3rd Ed): Chapter 18, PEGylation and Synthetic Polymer Modification," ProQuest ebrary 21:811-812 (Nov. 1, 2013).
Hermanson, "Bioconjugate Techniques (3rd Ed): Chapter 11, (Strept)avidin-Biotin Systems," ProQuest ebrary 21:493-495 (Nov. 1, 2013).
Roncato, "Preparation and Characterization of Ananas/Antibody/Drug Complexes: A First Comparative Investigation on Nanoparticle-based vs Antibody Conjugate Solutions for Targeted Drug Delivery," Padova Digital University Archive (Feb. 19, 2015) (abstract).

* cited by examiner

*Primary Examiner* — Yih-Horng Shiao
(74) *Attorney, Agent, or Firm* — Silvia Salvadori, P.C.; Silvia Salvadori (57) ABSTRACT

Nanoassembled complexes of nucleic acids, avidin and biotinylated compounds functionalized to make them suitable for delivering and releasing drugs are described. These nanoassembled complexes consist of central poly-avidin nucleus, i.e. nucleus formed from the self-assembling of tetrameric avidin units on oligonucleotide sequences of nucleic acids, on which biotinylated compounds are further auto-assembled through high-affinity interactions between the avidin of the central nucleus and the biotin of the biotinylated compounds. The biotinylated compounds are functionalized so as to bind drugs with a reversible bond, allowing the delivery thereof and a controlled release.

26 Claims, 3 Drawing Sheets

FIGURE 1

Biotinylated compounds (BC)

B-Xa-PAb (II)    PEG ending with fluorophore or methoxy targeting element B-Xa-PAb (III)   hydrazo-drug (spaced with PEG)

B-Xa (IV)        hydrazo-drug (short spacer)

hydrazide + carbonyl    hydrazone

NANOASSEMBLED COMPLEXES OF NUCLEIC ACIDS, AVIDIN AND BIOTINYLATED COMPOUNDS FOR USE AS DRUG CARRIERS

This application is a national stage application under 35 U.S.C. § 371 of PCT Application No. PCT/EP2016/066240, filed 8 Jul. 2016, which claims priority of Italy Application No. 102015000032694, filed 10 Jul. 2015, which are hereby incorporated by reference in their entirety.

FIELD OF THE INVENTION

The invention relates to nanoassembled complexes of oligonucleotide sequences of nucleic acids, avidin and biotinylated compounds, the latter functionalized for carrying and releasing drugs bound to the same by means of a reversible bond.

STATE OF THE ART

The development of technologies based on different types of nanoparticles is opening significant applications both in the therapeutic and in the diagnostic field. The objective pursued with the latest research is to develop multifunctional transport nanosystems that can deliver molecules with different functions (i.e. bioactive and/or tracing molecules) specifically to the desired anatomical site and in a more efficient manner. The technical problem is not only related to the ability to charge the various compounds to be delivered on the nanoparticles, but also to control their individual useful load in a reproducible and convenient manner. Particularly interesting in this context are nanocomplexes based on the high affinity interaction between avidin and biotin.

From the practical point of view, in fact, the property of avidin of having a high and multiple affinity for biotin represents the basis for its use as a molecular tool for a number of biotechnological applications. Due to this properties, avidin can in fact act as a molecular bridge to link together different biological or chemical units in a stable manner, with the proviso that the latter are covalently linked to a biotin molecule (Wilchek M and Bayer E A, 1988; Wilchek M and Bayer E A, 1990).

The most common applications of the avidin-biotin technology fall within the analytical field, more precisely in detection and quantification systems that are usually based on the possibility of binding an antibody, or any other molecule having high affinity towards the analyte (ligand/antigen), with a signal system (a fluorophore, an enzyme capable of emitting light/color, a radionuclide, etc.). Other applications include the functionalization of surfaces with specific chemical/biochemical entities, a procedure that is often conducted exploiting the molecular bridge consisting of the avidin:biotin complex.

In another application, drugs or diagnostic elements, administered parenterally, are directed to specific anatomical sites (Goldenberg D M et al., 2006).

One of the main limits of the traditional avidin:biotin technology, however, is the maximum number, equal to four, of biotines that can be bound to a single avidin molecule, which constitutes the central "nucleus" of the system, this being as known a tetrameric protein. The possibility of having a central nucleus able to bind more biotin molecules would theoretically increase the system potential.

This increased capacity can be achieved by binding together more avidin molecules in a unit definable as poly-avidin unit.

The substantial drive to the development of a poly-avidin technology derived from the discovery of the ability of avidin to also bind to nucleic acids with high-affinity interactions with the nucleobases of the same (Morpurgo M, et al. 2004). This led to the development of nanocomplexes formed by nucleic acids/avidin/biotin auto-assembled around a central nucleus consisting of a nucleic acid and multiple avidin units in a stoichiometric ratio between avidin and the pairs of nucleic bases equal to 1 (avidin) and 28 (nucleobases). The avidin assembled by affinity on the nucleic acid retains its ability to bind biotin with a stoichiometric ratio of 1:4 (avidin:biotin units), the avidin unit consisting of 4 subunits. In fact, the nucleic acid:avidin interactions involve specific regions of the protein, but do not involve the binding site for biotin which thus remains free to bind further biotinylated compounds, i.e. compounds derived from the covalent conjugation with biotin, according to the known avidin:biotin technology previously mentioned, by means of high affinity bonds.

The substantial problem of these nanoassembled complexes, however, is their poor stability with the formation of aggregates in aqueous saline environment, such as the physiological one.

In order to obviate this technical problem, which actually makes these nanoparticles unusable for therapeutic and/or diagnostic applications, nanoparticles derived from this double interaction nucleic acid:avidin and avidin:biotin, in which biotin binds by means a covalent bond a hydrophilic polymer able to ensure protection to the surface of these nanocomplexes, have been developed. These nanoassembled complexes are represented by the general formula $NB_n Av_y (B—X_a-PA_b)_z$ (NB=nucleobase; Av=avidin; B=biotin; X=linker; PA=hydrophilic polymer) (Morpurgo M et al, 2009; Pignatto M et al., 2010). This allowed obtaining nanoparticles, consisting of these nanocomplexes, which are soluble and stable in aqueous environment and which have a highly defined composition, being obtainable through high affinity interactions based on stoichiometric ratios between nucleobase:avidin:biotin.

These nanocomplexes have been compared with similar complexes based on the traditional avidin:biotin interaction in an in vitro analytical study based on immuno-detection and proved to be much more efficient in determining the analyte (Morpurgo M et al., 2012).

Recent studies carried out with nanoparticles that covalently bind two fluorophores have shown that the same following in vivo administration freely circulate in the bloodstream, have a time-dependent capacity to be internalized in the cells and are efficiently eliminated in 24-48 hours. These nanoparticles have also showed poor immunogenicity (Bigini P et al., 2014). These results make these nanoparticles interesting not only for use in the diagnostic but also in therapeutic field for drug administration.

In fact, a need deeply felt in the pharmaceutical industry is to develop advanced technologies of site-specific delivery and controlled release of drugs in order to improve the therapeutic index thereof.

It is therefore an object of the present invention to develop a system for the delivery and the controlled release of drugs based on the use of nanoparticles consisting of nanoassembled nucleic acids/avidin/biotinylated compounds.

SUMMARY

For this purpose, the inventors have set up nanoparticles of nanoassembled complexes of nucleic acids/avidin/biotinylated compounds in which the drug is bound to biotinylated compounds interacting with the binding site of biotin on avidin, so that they can be delivered and subsequently released by the same nanoparticles. The binding between the biotinylated compounds of the nanoassembled complexes and the drug to be delivered cannot therefore be a stable bond of covalent type but a reversible bond, although sufficiently stable to allow the nanoparticles to deliver the drug. The hydrazone linkage appears in this respect particularly interesting.

Therefore, in one aspect, the present invention refers to nanoassembled complexes comprising:
a) a nucleus consisting of an oligonucleotide sequence and one or more avidin units auto-assembled by means of high-affinity interactions between avidin and one or more nucleobases of the oligonucleotide sequence, and
b) biotinylated compounds assembled on biotin binding sites on the avidin of the nucleus by high-affinity interactions between avidin and biotin represented by the general formula (I)

$$NB_nAv_y(BC)_z \quad (I)$$

wherein:
NB are single nucleobases of the oligonucleotide sequence of a single or double stranded nucleic acid and n is a number higher than 16 and up to 100,000;
Av is a tetrameric avidin unit and y is an integer higher than or equal to 1 and being in relation to n it is in a range between (0.0001)·n and (0.0454)·n with the proviso that if (0.0001-0.0454)·n is less than 1, y is equal to 1;
BC are biotinylated compounds selected from compounds of formula:
B—$X_a$-$PA_b$ (II) where B is a biotin residue, X is a linker having at least two functionalizable residues and PA is a polymeric unit of a hydrophilic polymer having at least two functionalizable residues, one of which binds the biotin residue B with a covalent bond either directly or through the linker X by means of the carboxylic functional group thereof and the second is free or protected with protective groups or binds fluorophores or targeting molecules, a is a number comprised from 0 to 10, b is a number comprised from 1 to 20;
B—$X_a$-$PA_b$ (III) where B is a biotin residue, X is a linker having at least two functionalizable residues and PA is a polymeric unit of a hydrophilic polymer having at least two functionalizable residues, one of which binds the biotin residue B with a covalent bond either directly or through linker X by means of the carboxylic functional group thereof and the second is functionalized with a hydrazine residue selected from —R—C(=O)—NHNH$_2$, —R—O—C(=O)—NHNH$_2$, —R—NH—(C=O)—NHNH$_2$—R—NH—(C=S)—NHNH$_2$ e —R—(C$_6$H$_4$)—NHNH$_2$ where R is a linear or branched C$_1$-C$_{10}$ alkyl residue, a is a number comprised from 0 to 10, b is a number comprised from 1 to 20;
B—$X_a$ (IV) where B is a biotin residue, X is a linker having at least two functionalizable residues, one of which binds the biotin residue B with a covalent bond directly by means of the carboxylic functional group thereof and the second is functionalized with a hydrazine residue selected from —R—C(=O)—NHNH$_2$, —R—O—C(=O)—NHNH$_2$, —R—NH—(C=O)—NHNH$_2$—R—NH—(C=S)—NHNH$_2$ and —R—(C$_6$H$_4$)—NH—NH$_2$ where R is a linear or branched C$_1$-C$_{10}$ alkyl residue, a is a number comprised from 1 to 10, and z is an integer higher than or equal to 1 and being in relation to y it is comprised from (0.02)·y to (4)·y with the proviso that if (0.02-4)·y is less than 1, z is equal to 1, with the proviso that the biotin binding sites on avidin of the NB$_n$Av$_y$ nucleus are saturated by at least 5% with biotinylated compounds of formula B—$X_a$-$PA_b$ (II) and/or (III), and wherein the biotinylated compounds of formula (III) and/or (IV) are conjugated with a hydrazone linkage —NH—N= with bioactive molecules having at least one carbonyl group.

Therefore, in another aspect, as a further object of the invention, hydrazonic conjugated of nanoassembled complexes of general formula (I) are provided, in which the biotinylated compounds of formula (III) and/or (IV) functionalized with hydrazine residues are conjugated by a hydrazone linkage with bioactive molecules having a carbonyl group.

Yet in another aspect, another object of the invention relates to the use of nanoassembled complexes of general formula (I) as carrier to deliver bioactive molecules.

The advantages provided by the present invention will become readily apparent to one skilled in the art from the following detailed description of particular embodiments, given by way of non-limiting example, and with reference to the following figures.

DETAILED DESCRIPTION OF THE INVENTION

Definitions

The terms "nanocomplexes", "nanoassembled" and "nanoassembled compounds" are used to denote the complexes obtained by a dual auto-assembly. The first auto-assembly occurs by high-affinity interactions between the nucleobases (NB) of an oligonucleotide sequence of a single or double stranded nucleic acid and one or more units of the tetrameric protein avidin (Av), hereinafter also referred to as avidin unit, and leads to the formation of a central nucleus NB$_n$Av$_y$. The second auto-assembly is between the avidin of the central nucleus NB$_n$Av$_y$ obtained from the first auto-assembly NB:Av and biotin (B) of one or more biotinylated compounds BC that auto-assemble on the nucleus NB$_n$Av$_y$ by high-affinity interactions on the biotin binding sites to avidin. Such auto-assembled complexes are in the form of toroidal nanoparticles, therefore they are also referred to herein as "nanoparticles" (briefly NP).

The term "nucleic acid(s)" refers to single- or double-chain nucleic acids consisting of any sequence of a single- or double-stranded deoxyribonucleic acid (DNA), any sequence of a ribonucleic acid (RNA) as a single-stranded or hybridized with a complementary RNA or DNA chain, or a sequence of these nucleic acids in which a portion or all of the bases have been chemically modified which may be in linear or circular form, in relaxed, coiled or supercoiled state.

The term avidin is meant to denote the tetrameric protein, both native from hen eggs or other similar source (volatile eggs in general) and recombinant both in the glycosylated and de-glycosylated form. Also other forms of chemically or genetically modified avidin are contemplated, with the proviso that they are able to auto-assemble on an oligonucleotide sequence of both single and double stranded nucleic acid as defined above.

By dendrimer it is meant a symmetrical macromolecular compound consisting of branches repeated around a central nucleus consisting of a smaller molecule with multiple functional groups, or a polymeric nucleus. The functional groups present on the surface of the dendrimer, the number of which depends on the number of branches thereof, are in turn functionalizable with other molecules including, for example, polymers PA.

In the nanoassembled complexes of the present invention, the polymeric units PA are biocompatible and hydrophilic polymers and are known polymers (Owens D E and Peppas N A, 2006). Such polymeric units are selected from the group consisting of polyethylene oxide or polyethylene glycol (PEO or PEG) optionally also substituted, a polyoxyethylene and polyoxypropylene (PEO-PPO) copolymer, polyvinylpyrrolidone (PVP), poly acryloyl morpholine (PacM), a polyoxamine, a poly-lactic acid (PLA), a polyglycolic (PLG), a lactic acid and glycolic acid (PLGA) copolymer.

The terms "binder", "linker" and "spacer" used herein are to be deemed equivalent for the purposes of the present description of the invention.

Even when not specifically indicated, the term "coating agent" or "protective agent" is to be understood as referred to BC biotinylated compounds, in which polymer PA is present for the purpose of safeguarding the stability of the complexes in saline environment irrespective of its functionalization on the second functional group. These biotinylated compounds may be either compounds of formula B—$X_a$-$PA_b$ (II) and/or (III).

The term "targeting element" refers to molecules able to direct the functionalized nanoparticles by directing them towards the target site for therapeutic treatment. The term therefore includes ligands for specific receptors or antigens, such as antibodies for a specific antigen, folic acid for its receptor or sugars such as galactose for its hepatic receptors.

Description

The nanoassembled complexes of general formula (I) $NB_n Av_y (BC)_z$, wherein NB, Av, BC and n, y and z have the meanings mentioned above, have a well-defined composition based on the stoichiometric ratios between NB:Av:B and are in the form of discrete nanoparticles in terms of size, in which protection and stability in a saline environment, such as the physiological one, of the central nucleus NB $Av_y$ is ensured by the hydrophilic polymers present on the surface.

Compared to the prior art, these nanoassembled complexes $NB_n Av_y (BC)_z$ mentioned above have the peculiarity of comprising in all cases biotinylated compounds of formula (III) and/or (IV), both respectively equal to or different from each other, characterized in that they have a hydrazine residue selected from: a hydrazide —R—C(=O)—$NHNH_2$, a carboxylated hydrazine —R—O—C(=O)—$NHNH_2$, a semicarbazide —R—NH—C(=O)—$NHNH_2$, a thiosemicarbazide —R—NH—C(=S)—$NHNH_2$ and an aryl hydrazine —R—($C_6H_4$)—$NHNH_2$, wherein R is a linear or branched $C_1$-$C_{10}$ alkyl residue.

The biotinylated compounds BC can therefore be selected from compounds of formula (III) B—$X_a$-$PA_b$ when the functionalization is on a polymer PA, or of formula (IV) B—$X_a$ when the hydrazine functionalization is on a spacer that binds biotin. Irrespective of whether such different functionalization is on a second functional group of the PA hydrophilic polymer or on an at least bifunctional spacer binding a biotin by the carboxyl thereof, this allows the conjugation by a hydrazone linkage of a bioactive molecule which has at least one aldehyde or ketone carbonyl according to the reaction:

$$R^1\underset{H}{\overset{}{N}}-NH_2 + \underset{R^2}{\overset{O}{\underset{\|}{C}}}R^3 \rightleftharpoons R^1\underset{H}{\overset{H}{N}}-\underset{OH}{\overset{N}{\underset{|}{C}}}\underset{R^2}{\overset{R^3}{}} \rightleftharpoons R^1\underset{H}{\overset{}{N}}-N=\underset{R^2}{\overset{R^3}{C}}$$

The hydrazone bond is reversible, since it may be subject to a double bond hydrolysis process to acid pH and also up to physiological pH around 7.4.

In any case, however, in order to ensure the stability of these nanoassembled, the requirement that at least 5% of the biotin binding sites on the avidin of core $NB_n Av_y$ is saturated with biotinylated compounds bearing a polymer PA of formula B—$X_a$-$PA_b$, equal or different from each other irrespective of the functionalization of the polymer PA, is an essential requirement as regards the stability of the nanocomplex in aqueous saline environment.

Therefore, in a first embodiment, the nanoassembled complexes of general formula (I) have biotinylated compounds of formula (III) B—$X_a$-$PA_b$, equal or different from each other, where the PA hydrophilic polymer is functionalized with hydrazine residues, are also, irrespective of the functionalization thereof, surface protecting agents. Assumed that the polymeric unit PA is a polyethylene glycol (PEG), a polymer that for the purposes of the present invention is preferable together with its copolymer with polyoxypropylene (PEG-PPO), when the polymer PA has a hydrazine functionalization, depending on this functionalization the biotinylated compound can be of formula:

B—C(=O)—$X_a$—($CH_2CH_2$—O)$_m$—R—C(=O)—$NHNH_2$      (V),

B—C(=O)—$X_a$—($CH_2CH_2$—O)$_m$—R—O—C(=O)—$NHNH_2$      (VI), B—C(=O)—$X_a$—($CH_2CH_2$—O)$_m$—R—NH—C(=O)—$NHNH_2$      (VII), B—C(=O)—$X_a$—($CH_2CH_2$—O)$_m$—R—NH—C(=S)—$NHNH_2$      (VIII), B—C(=O)—X$_a$—(CH$_2$CH$_2$—O)$_m$—R—(C$_6$H$_4$)—NHNH$_2$  (IX).

The biotinylated compounds of formula (V) and (VI) are preferred for the purposes of the present invention and preferably R is between 2 and 10 and more preferably is between 2 and 6.

Such biotinylated compounds can deliver the same or different molecules, selected from bioactive molecules for therapeutic use, having a ketone or aldehyde carbonyl group, bound by a hydrazone linkage to the polymer PA of the coating agent B—X$_a$-PA$_b$.

The biotinylated compound of formula B—X$_a$-PA$_b$ conjugated with a hydrazone linkage to a drug Z can therefore be represented by the general formulas:

B—C(=O)—X$_a$—(CH$_2$CH$_2$—O)$_m$—R—C(=O)—NHN=Z  (Va),

B—C(=O)—X$_a$—(CH$_2$CH$_2$—O)$_m$—R—O—C(=O)—NHN=Z  (VIa),

B—C(=O)—X$_a$—(CH$_2$CH$_2$—O)$_m$—R—NH—C(=O)—NHN=Z  (VIIa),

B—C(=O)—X$_a$—(CH$_2$CH$_2$—O)$_m$—R—NH—C(=S)—NHN=Z  (VIIIa),

B—C(=O)—X$_a$—(CH$_2$CH$_2$—O)$_m$—R—(C$_6$H$_4$)—NHN=Z  (IXa).

A significant feature of these nanoparticles is, however, related to the fact that the biotin binding sites present on the avidin units of the central nucleus (NB)$_n$Av$_y$, cannot be completely saturated by the biotinylated surface protecting agent B—X$_a$-PA$_b$ of formula (II) and/or (III) for reasons arising from both preparative and physical choices.

In the first case, the incomplete saturation of the biotin binding sites on avidin is a direct consequence of the stoichiometric ratios between the avidin units and the biotins of the protecting agent used in the preparation of the nanoassembled compounds and therefore is a condition pursued in the preparation of the same nanoparticles.

In the second case, instead, the presence free biotin binding sites on the avidin units of the central nucleus can be a consequence of the steric effects of the polymers of the coating agents present on the surface of nanoparticles, which may block the access of other coating agents B—X$_a$-PA$_b$ to the same.

In any case, this leaves biotin binding sites on the avidin free for further high-affinity interactions between the avidin units and other biotinylated compounds, different from the protecting agent B—X$_a$-PA$_b$, capable of penetrating the nanoparticles, despite the presence of the polymers of the coating agents on the surface. This second biotinylated compound can be included in the nanoparticles by adsorption processes facilitated by the high affinity between avidin and biotin of the nanoassembled complex NB$_n$Av$_y$(BC)$_z$.

Figure 3:
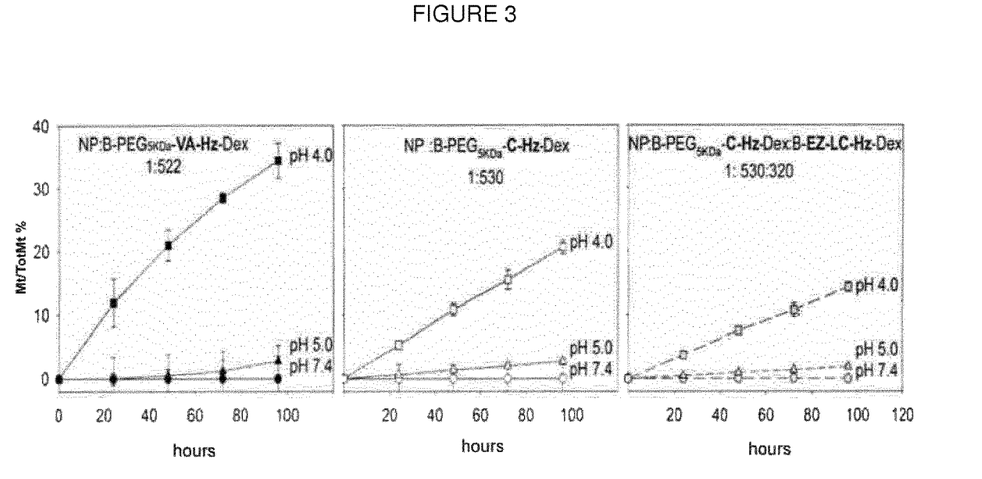
FIG. 3. The figure shows the results of the release kinetics of dexamethasone from the nanoassembled complexes of examples 2, 3, 4, as a function of time and pH.

This, therefore, allows delivering molecules, either equal to or different from each other, selected from bioactive molecules for therapeutic use by binding them by means of a hydrazone linkage to a functionalized spacer of a further biotin different from that of the coating agent.

Therefore, in a second embodiment of these nanoparticles usable as carriers, the free biotin binding sites can be saturated with biotinylated compounds of formula (IV), wherein the biotin can bind through a linker X a residue with a hydrazine function through which conjugate with a hydrazone bond bioactive molecules for therapeutic use, which have a ketone or aldehyde carbonyl group, equal to or different from each other. These biotinylated compounds can be represented for example by the general formulas:

$B—C(=O)—X_a—R—C(=O)—NHNH_2$ X), $B—C(=O)—X_a—R—O—C(=O)—NHNH_2$ (XI), $B—C(=O)—X_a—R—NH—C(=O)—NHNH_2$ (XII), $B—C(=O)—X_a—R—NH—C(=S)—NHNH_2$ (XIII), $B—C(=O)—X_a—R—(C_6H_4)—NHNH_2$ (XIV)

and the conjugated compounds thereof with a hydrazone bond to a drug Z with the general formulas:

$B—C(=O)—X_a—R—C(=O)—NHN=Z$ (Xa), $B—C(=O)—X_a—R—O—C(=O)—NHN=Z$ (XIa), $B—C(=O)—X_a—R—NH—C(=O)—NHN=Z$ (XIIa), $B—C(=O)—X_a—R—NH—C(=S)—NHN=Z$ (XIIIa), $B—C(=O)—X_a—R—(C_6H_4)—NHN=Z$ (XIVa).

Also in this case, the biotinylated compounds of formula (X) and (XI) are preferred for the purposes of the present invention and preferably R is between 2 and 10 and more preferably is between 2 and 6.

In this second embodiment, the biotinylated coating agent can be of formula (II) and or (III). In this latter case, the biotinylated compound has both the function of the nanoparticle surface protection and that of carrying conjugated bioactive molecules linked by a hydrazone bond.

This feature is very important for therapeutic application purposes, as it allows designing and preparing nanoparticles according to the therapeutic needs pursued with a modulated and controlled release of drugs conjugated to the biotinylated compounds, whether they are the surface protecting agent or further biotinylated compounds that do not bind polymers.

In fact, if the drug is conjugated to the polymer PA of the surface protecting agent $B—X_a\text{-}PA_b$, as this is exposed on the surface of the nanoparticle, it will undergo hydrolytic processes more rapidly compared to a drug conjugated to biotinylated compounds represented by the general formula (IV) devoid of the surface coating polymer PA, and thus internalized in the nanoparticle.

In this case, in fact, in addition to protecting the nanoparticles, the coating agent $B—X_a\text{-}PA_b$, can also protect the biotinylated compounds conjugated to the drug according to one of formulas (Xa) to (XIVa) and allow a sustained release thereof over time, while the drug conjugated to the polymer according to one of formulas (Va) to (IXa) can be subjected to a quick release. Indeed, as shown in FIG. 3 (second and third panel) and table 1, we unexpectedly found that when the nanoparticles were functionalized with only the biotin-hydrazone derivative of dexamethasone of formula (VIa), or with a mixture of two biotin hydrazones of formulas (VIa) and (Xa), the kinetics of drug release, expressed as % of dexamethasone released over the total dexamethasone drug in the NP, was different. In particular, release was faster (15.4% release after 72 h at pH 4.0) when testing the NPs with the derivative (VIa) (Dex:NP=530) as compared to when using the mixture (VIa):(Xa):NP 530:320:1 (10.6% release at 72 h). This difference can only be explained by the fact that the two hydrazones of dexametasone have different hydrolytical stability. Since dexametasone derivative (VIa) has the same atom in alpha position to the hydrazone function as derivative (Xa) which leads to less hydrolytically stable NPs (FIG. 3, panel 1), the unexpected difference observed between the kinetics of panel 2 and 3 of FIG. 3 is likely due to the different proximity of the hydrazone functions to the NP core. The latter probably generates a different chemical environment. and causes the unexpected slowering of the release kinetic.

Figure 4:
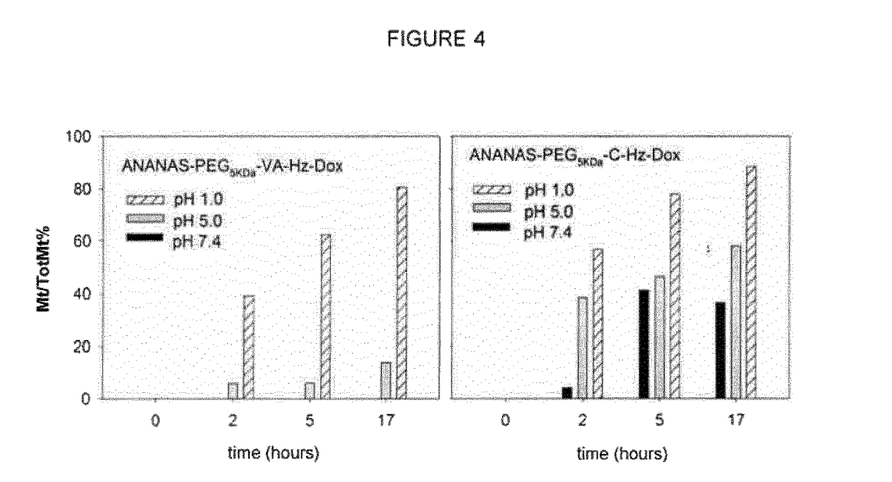
FIG. 4. The figure shows the results of the release kinetics of doxorubicin from the nanoassembled complexes of example 7, as a function of time and pH.

In fact, and again unexpectedly, when comparing drug hydrazone derivatives of formula (III) we found that the nature of the atom adjacent (in alpha) to the hydrazide unit of the biotin linker influences the hydrolytic stability of the drug-hydrazone bond, so that, for example, it is possible to generate different release kinetics from the nanoparticles by loading them with reagents of formula (Va) or (VIa) or (VIIa) or (VIIIa). In fact, by comparing panels 1 and 2 of FIG. 3, we observe that dexametasone release from nanoparticles formulated with the hydrazone of formula (Va) (example 2) is faster (28% release at 72 h at pH 4.0) than that obtained from nanoparticles formulated with hydrazone of formula (VIa) (example 3) (15% release after 72 h at pH 4.0). The same data are summarized in table 1. Also, as shown in FIG. 4, the release of doxorubicin (example 7) from NPs formulated with the hydrazone drug derivative of formula (Va) is faster (40% release after 5 h at pH 7.4), specially at pH 7.4, than that from the formulation obtained with derivative (VIa) (0% release after 5 h at pH 7.4). It is also important to note that, again unexpectedly, we could not identify a unique rule dictating the relative hydrolytical stability of the hydrazones based on the nature of the atom in alpha position of the drug-free biotin-hydrazide. For example, the dexametasone derivative of (Va) is less hydrolytically stable that derivative (VIa), while the doxorubicin derivative of (Va) is more stable that of derivative (VIa).

In this second embodiment, the nanoparticles can be used as multiple and/or differentiated release carriers of bioactive molecules bound to the protecting agent polymer or directly via a linker to a biotin, respectively. In fact, since the bioactive molecules bound to the polymer are exposed on the surface of the nanoparticle, they can be more easily and quickly subject to degradation processes, while for molecules directly or indirectly through a linker bound to biotin and assembled on the avidin of the central nucleus, a slower release kinetics can be contemplated.

In another embodiment can be prepared nanoparticles $NB_n Av_y (BC)_z$ wherein the biotinylated compounds are compounds of formula (II) and, therefore, the polymer PA is not conjugated with molecules for therapeutic use and has only protection functions of the nanoparticle surface, and wherein the biotin binding sites are not saturated by these coating agents $B—X_a-PA_b$. In this case, the nanoparticle delivery function is fulfilled by biotinylated compounds conjugated to molecules for therapeutic use can be represented by the general formulas (Xa) to (XIVa).

In further embodiments, the polymer PA of the biotinylated compounds of formula (II) can also be bound via covalent bonds with fluorophores and/or targeting elements that allow targeting the drug to the site (such as, tumor cells) and/or verifying the drug distribution after administration.

Figure 1:
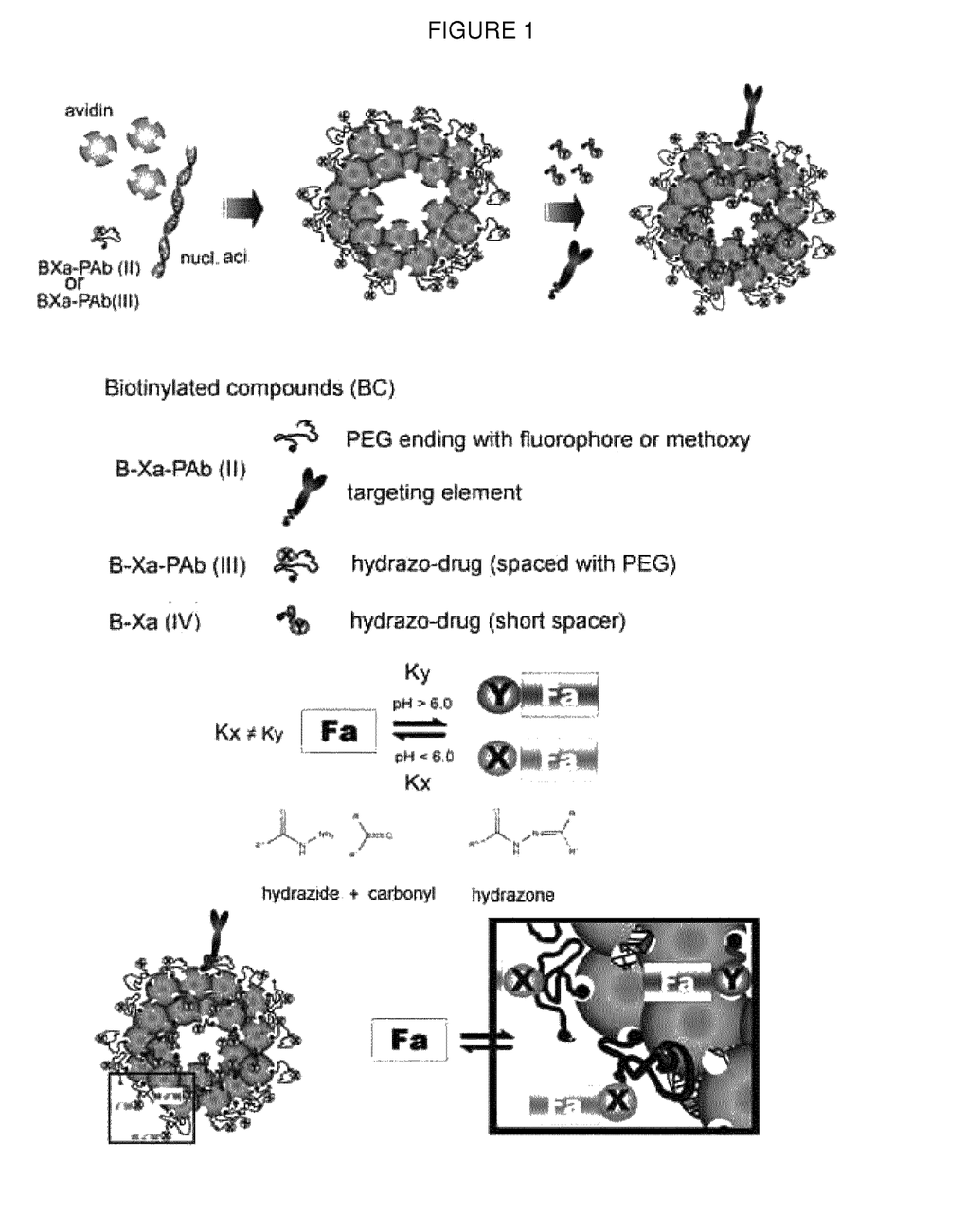
FIG. 1. The figure shows the assembly scheme of nanoparticles starting from the different components (avidin, nucleic acid and biotinylated coating and functionalization agents), and pH-dependent modular drug release mechanism from the hydrazine bond.

From these examples of possible embodiments of these nanoparticles, of which FIG. 1 shows an exemplary graphical representation, the extreme versatility and simplicity of preparation thereof can be inferred.

For the purposes of the present invention, nanoparticles with predetermined compositions are preferred, in which the components $NB_n$, $Av_y$ and $BC_z$ have the meanings specified hereinafter.

In a preferred embodiment, $NB_n$ is a nucleic acid where n is comprised from 30 to 50,000 and, consequently, y is comprised from 1 to 1785 and z is comprised from 1 to 7140. More preferably, n is comprised from 3,000 to 20,000 and, consequently, y is comprised from 30 to 714 and z is comprised from 120 to 2850. Preferably, y is comprised from (0.01)•n to (0.0454)•n and z is comprised from (0.4)•y to (4)•y.

In the biotinylated compounds BC, a is preferably comprised from 0 to 5 for biotinylated compounds of formula (II) or (III) and from 1 to 5 for biotinylated compounds of formula (IV) and when a is different from 0, and thus the linker X present, this linker X is a spacer of general formula (XV) $Y—R^1—Y^1$, wherein:

Y, Y' equal to or different from each other are —COO—, —NH—, —O—; —SO$_2$—, —S—, —SO—, —CO—, —COS—; —NH—CO—, —NH—COO—, —HN—SO—NH—;

$R^1$ is alkyl, alkenyl, alkynyl, cycloalkyl and aryl, with a carbon atom number comprised from 1 to 20, and preferably from 5 to 10, optionally substituted.

Therefore, the linkage between the linker X and biotin B and that between the linker X and the hydrophilic polymer PA can without distinction be an amide bond, an amine bond, a carbamide bond, an ester bond, a ketone bond, an ether bond, a thioester bond, a thioether bond, an urea bond, a thiourea, a sulfonic and a sulfoxide bond.

More preferably, the linker X is a spacer group wherein Y and Y' are —NH—CO— and —NH—COO— and $R^1$ is a linear alkyl with 6-8 carbon atoms.

When the linker X has more than two functional groups, and in particular a number of functional groups equal to or higher than 3 (≥3) of which one is bound to biotin and the other free for different conjugations, these further functional groups can be functionalized with hydrazine residues, in the case of biotinylated compounds of formula (IV) or bind multiple polymer units, in the case of biotinylated compounds of formula (II) and/or (III).

In fact, when b is higher than 1 and then PA represents a hydrophilic polymer consisting of at least 2 or more polymeric units, the latter are bound together by a different linker X having a number of derivatizable functionalities equal to or higher than 3 (≥3), of which one binds biotin and the other functional groups bind the polymeric units PA when a is different from 0 or, when a is equal to 0 and then the linker X is not present, a first polymeric unit PA binds directly biotin B through its carboxy group and the remaining polymeric units PA are bound to the first polymeric unit binding biotin.

Such a different linker X can be selected from lysine, glutamic acid, aspartic acid, cysteine, a dendrimer. For the purposes of the present invention, this further polyfunctional linker is preferably lysine.

With reference to the hydrophilic polymer PA, for the purposes of the present invention, the preferred polymers are selected from polyethylene glycol (PEG), also optionally substituted, or a copolymer thereof with polyoxypropylene (PPO) and the polymeric unit PA has a molecular weight of comprised from 400 to 20,000 and more preferably between 1,000 and 5,000 and b is preferably comprised from 1 to 10.

With regard to bioactive molecules or drugs that can be conjugated to biotinylated compounds of formula (III) or (IV), they should have at least one aldehyde or ketone carbonyl group available for the conjugation with the hydrazine residue of the biotinylated compounds. Among them, both corticosteroid and non-steroidal anti-inflammatory agents, anticancer, antibiotics, antigout agents are preferred. Corticosteroid anti-inflammatory agents are preferably selected from hydrocortisone, dexamethasone, triamcinolone, triamcinolone acetonide, triamcinolone diacetonide, prednisolone, methyl prednisolone and salts thereof. Non-steroidal anti-inflammatory agents are preferably selected from droxicam, tenoxicam, lornoxicam, ketoprofen, tolmetin, nabumetone, ketorolac and salts thereof.

Among the anti-cancer agents, these are preferably selected from doxorubicin, daunomycin, epirubicin, idarubicin, paclitaxel, docetaxel, carbazitaxel, cyproterone and salts thereof.

Antibiotics are preferably selected from doxycycline, chlortetracycline, erythromycin, oleandomycin, clarithromycin, flurithromycin and salts thereof. Among antigout agents, colchicine and salts thereof is preferably selected.

The conjugated derivatives according to the invention can be used for the treatment of elective diseases of the delivered bioactive molecule. Preferably, these diseases are diseases characterized by acute and chronic inflammatory processes, and preferably these are osteoarticular diseases such as arthritis and osteoarthritis and autoimmune diseases of different etiology and affecting different anatomical areas or organs, cancer or infectious diseases and gout.

The nanoparticles according to the invention have shown an excellent biocompatibility profile and can therefore be used for the preparation of compositions in combination with known and/or novel diluents and/or excipients acceptable for therapeutic treatments. The administration routes usable for these therapeutic treatments are all those known, general or local site-specific, and used in clinical practice, typical for the delivered drug and the disease to be treated. In particular, for the osteoarticular pathologies treated with anti-inflammatory agents, the administration route to be preferred is intraarticular and the conjugated nanoparticles according to the invention can be incorporated into compositions in combination with polysaccharides such as hyaluronic acid, alginic acid, chitosan and oligosaccharide derivatives thereof or mixtures thereof.

Such compositions may be used alone or in combination with compositions comprising the drugs delivered by the nanoparticles and as such, namely not delivered by the nanoparticles, according to the therapeutic regimen necessary for treating the disease.

Figure 2:
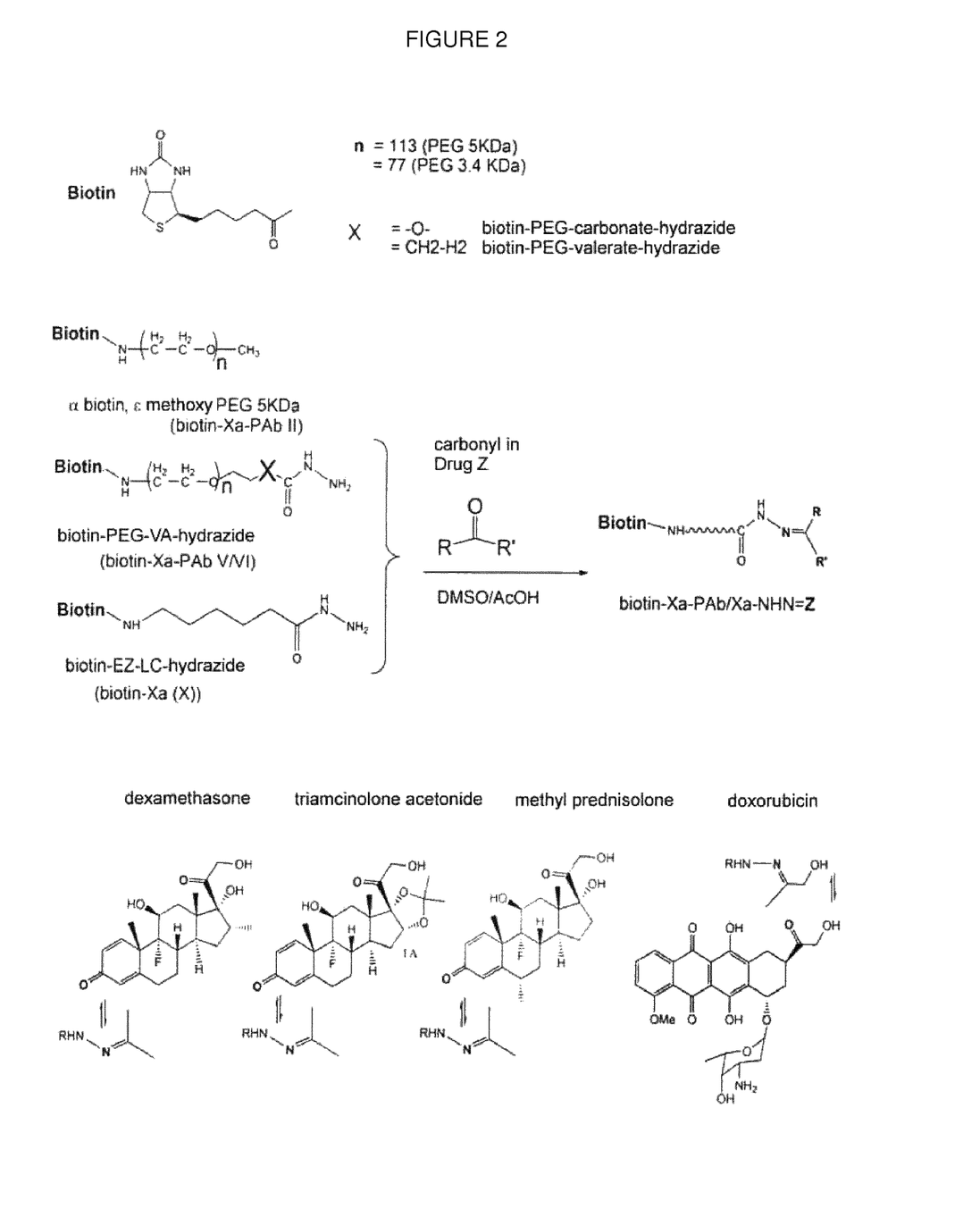
FIG. 2. The figure shows the biotinylated compounds indicated in examples 2-9.

Some examples of preparation of the nanoassembled compounds according to the invention are described hereinafter for non-limiting illustrative purposes, which for more clarity are shown in FIG. 2, and their characterization for the release kinetics of derivatives conjugated with a hydrazone bond.

EXAMPLES

Example 1. Synthesis of Biotin-PEG-VA-Hydrazide (5 KDa) and Biotin-PEG-C-Hydrazide (5 KDa and 3.4 KDA) Biotinylated Compounds The three biotinylated PEG derivatives were obtained starting from biotin-PEG-succinimidyl-valerate (5 KDa) or biotin-PEG-succinimidyl carbonate (5 KDa or 3.4 KDa) (Laysan Bio) respectively, mixing the active esters with 4 equivalents of tert-butyl carbazate (BOC-Hz, Sigma-Aldrich) in a mixture of 1:1 anhydrous ethyl acetate and dichloromethane, followed by 1 equivalent of triethylamine. After 1 hour, the conjugation products were isolated by precipitation in ethyl ether and purified from the excess of tert-butyl carbazate through a series of re-dissolutions and precipitations with ethyl acetate and ethyl ether. The conjugation of the carboxylic residue of the various derivatives with BOC-hydrazide was confirmed by $^1$H-NMR analysis.

The BOC protecting group was, then, removed by acid treatment with by 95% TFA in water and the products were isolated by crystallization in cold anhydrous ethyl ether. The complete removal of BOC was confirmed by $^1$H-NMR analysis.

Example 2. Synthesis of Nanoparticles with Biotinylated Compounds of Formula B—$X_a$-$PA_b$ (III) Functionalized with Dexamethasone Via $PEG_{5KDa}$-Valerate-Hydrazone ($PEG_{5KDa}$-Va-Hz-Dex) Linker The biotin-PEG-VA-hydrazo-dexamethasone (B-$PEG_{5KDa}$VA-Hz-DEX) conjugate was obtained by mixing biotin-$PEG_{5KDa}$-VA-hydrazide (example 1) in the presence of two equivalents of dexamethasone (DEX) in anhydrous dimethylsulfoxide, acid for acetic acid. The formation of the hydrazone was followed by titrating the free hydrazide groups with the trinitrobenzene sulfonic (TNBS) reagent. When the reaction was complete, the product was isolated by precipitation in ethyl ether. The DEX excess was removed by successive washes with ethyl ether, and the product dried under vacuum. The product identity (hydrazone at C3 of DEX) was confirmed by $^1$H-NMR.

Nanoassembled (NP) consisting of avidin+pEGFp plasmid were obtained by mixing the two reagents in an aqueous medium and stabilized in the presence of α-biotin, ε-methoxy $PEG_{5KDa}$ so as to saturate 12.5% of the biotin binding sites. After purification by gel filtration (Superose column, in FPLC Akta purifier system) in 10 mM phosphate buffer eluent, 0.15 M NaCl, the nanoassembled NB:Av:B-ε-methoxy$PEG_{5KDa}$ (hereinafter referred to as ANANAS) was admixed with B-$PEG_{5KDa}$-VA-Hz-DEX at a 1:1 ratio to the biotin binding sites. After 1 hour, the mixture was purified again by gel filtration. In order to titrate the number of DEX/NP molecules, the assembled was treated with 0.1 M HCl for 3 h at 50° C. and the released DEX was quantified by HPLC analysis (C18 column, water/acetonitrile/TFA eluents). The assembled (ANANAS:B-$PEG_{5KDa}$-VA-Hz-DEX) was found to contain 522 DEX/NP molecules.

Example 3. Synthesis of Nanoparticles with Biotinylated Compounds of Formula B—$X_a$-$PA_b$ (III) Functionalized with Dexamethasone Via $PEG_{5KDa}$-Carbonate-Hydrazone ($PEG_{5KDa}$-C-Hz-DEX) Linker The biotin-PEG-C-hydrazo-dexamethasone (B-$PEG_{5KDa}$-C-Hz-DEX) conjugate was obtained by mixing biotin-hydrazide (example 1) in the presence of two equivalents of dexamethasone (DEX) in anhydrous dimethylsulfoxide, acid for acetic acid. The formation of the hydrazone was followed by titrating the free hydrazide groups with the trinitrobenzene sulfonic (TNBS) reagent. When the reaction was complete, the product was isolated by precipitation in ethyl ether. The DEX excess was removed by successive washes with ethyl ether, and the product dried under vacuum. The product identity (hydrazone at C3 of DEX) was confirmed by $^1$H-NMR.

A nanoassembled (NP) consisting of avidin+pEGFp plasmid and α-biotin, ε-methoxy $PEG_{5KDa}$ (12.5% of the binding sites for biotin-BBS) was obtained and purified as indicated in example 2, and admixed with the B-$PEG_{5KDa}$-C-Hz-Dex conjugate in the ratio of 0.5:1 to the biotin binding sites. After 1 hour, the mixture was purified again by gel filtration. In order to titrate the number of DEX/NP molecules, the assembled was treated with 0.1 M HCl for 3 h at 50° C. and the released DEX was quantified by HPLC analysis (C18 column, water/acetonitrile/TFA eluents). The assembled (ANANAS:B-PEG$_{5KDa}$-C-Hz-DEX) was found to contain 530 DEX/NP molecules.

Example 4. Synthesis of Nanoparticles with Double Functionalization, Using Biotinylated Compounds of Formula B—X$_a$-PA$_b$ (III) Functionalized with Dexamethasone (DEX) Via PEG$_{5KDa}$ Carbonate-Hydrazone (PEG$_{5KDa}$-C-Hz-DEX) Linker and of Formula B—X$_a$ (IV) Via EZ-LC Hydrazone (EZ-LC-Hz-DEX) Linker The biotin-EZ-LC-Hz-DEX conjugate was obtained by mixing biotin-EZ-LC-hydrazide (Pierce) in the presence of 1.2 equivalents of dexamethasone (DEX) in anhydrous dimethylsulfoxide acid for acetic acid. The formation of the hydrazone was followed by titrating the free hydrazide groups with the trinitrobenzene sulfonic (TNBS) reagent. When the reaction was complete, the product was isolated by precipitation in ethyl ether. The product identity (hydrazone at C3 of DEX) was confirmed by $^1$H-NMR.

The assembled ANANAS:B-PEG$_{5KDa}$-C-Hz-DEX was obtained as indicated in example 3. The nanoassembled were then added to the biotin-EZ-LC-Hz-DEX derivative in a molar ratio biotin:biotin binding sites of 0.4:1. After 1 hour, the mixture was purified again by gel filtration. In order to titrate the number of DEX/NP molecules, the assembled was treated with 0.1 M HCl for 3 h at 50° C. and the released DEX was quantified by HPLC analysis (C18 column, water/acetonitrile/TFA eluents). The assembled (ANANAS:B-PEG$_{5KDa}$-VA-Hz-C-DEX:B-EZ-LC-Hz-DEX) was found to contain about 850 DEX/NP molecules.

Example 5. Synthesis of Nanoparticles with Biotinylated Compounds of Formula B—X$_a$-PA$_b$ (III) Functionalized with Triamcinolone Acetonide Via PEG$_{3.4KDa}$-Carbonate-Hydrazone (PEG$_{3.4KDa}$ C-Hz-TA) Linker The biotin-PEG-C-hydrazo-triamcinolone acetonide (B-PEG$_{3.4KDa}$C-Hz-TA) conjugate has been obtained by mixing biotin-PEG$_{3.4KDa}$C-hydrazide (example 1) in the presence of two equivalents of triamcinolone acetonide (TA) in anhydrous dimethylsulfoxide, acid for acetic acid. The formation of the hydrazone was followed by titrating the free hydrazide groups with the trinitrobenzene sulfonic (TNBS) reagent. When the reaction was complete, the product was isolated by precipitation in ethyl ether. The TA excess was removed by successive recrystallizations from warm/cold ethyl acetate and washes with ethyl ether, and the product dried under vacuum. The product identity (hydrazone at C3 of TA) was confirmed by $^1$H-NMR.

A nanoassembled (NP) consisting of avidin+pEGFp plasmid and α-biotin, ε-methoxy PEG$_{5KDa}$ (12.5% of the binding sites for biotin-BBS) was obtained and purified as indicated in example 2, and admixed with the B-PEG$_{3.4KDa}$ C-Hz-TA derivative in the ratio of 1:1 to the biotin binding sites. After 1 hour, the mixture was purified by gel filtration. In order to titrate the number of TA/NP molecules, the assembled was treated with 0.1 M HCl for 3 h at 50° C. and the released TA was quantified by HPLC analysis (C18 column, water/acetonitrile/TFA eluents). The assembled (ANANAS:B-PEG$_{3.4KDa}$-C-Hz-TA) was found to contain about 790 molecules of TA/NP.

Example 6. Synthesis of Nanoparticles with Biotinylated Compounds of Formula B—X$_a$-PA$_b$ (III) Functionalized with Triamcinolone Acetonide (TA) Via PEG$_{5KDa}$-Valerate-Hydrazone (PEG$_{5KDa}$-VA-Hz-TA) Linker The biotin-PEG-VA-hydrazo-triamcinolone acetonide (B-PEG$_{5KDa}$-VA-Hz-TA) conjugate was obtained by mixing biotin-PEG$_{5KDa}$-VA-hydrazide (example 1) in the presence of two equivalents of TA in anhydrous dimethylsulfoxide, acid for acetic acid. The formation of the hydrazone was followed by titrating the free hydrazide groups with the trinitrobenzene sulfonic (TNBS) reagent. When the reaction was complete, the product was isolated by precipitation in ethyl ether. The TA excess was removed by successive recrystallizations from warm/cold ethyl acetate and washes with ethyl ether, and the product dried under vacuum. The product identity (hydrazone at C3 of TA) was confirmed by $^1$H-NMR.

Nanoassembled (NP) consisting of avidin+pEGFp plasmid were obtained by mixing the two reagents in an aqueous medium and stabilized in the presence of B-PEG$_{5KDa}$-VA-Hz-TA so as to saturate 100% of the biotin binding sites. The nanoassembled was purified by gel filtration (Superose column, in FPLC Akta purifier system) in 10 mM phosphate buffer eluent, 0.15 M NaCl. In order to titrate the number of TA/NP molecules, the assembled was treated with 0.1 M HCl for 3 h at 50° C. and the released TA was quantified by HPLC analysis (C18 column, water/acetonitrile/TFA eluents). The assembled, in which the biotinylated compounds are all B-PEG$_{5KDa}$-VA-Hz-TA, was found to contain about 670 molecules of TA/NP.

Example 7. Synthesis of Nanoparticles with Biotinylated Compounds of Formula B—X$_a$-PA$_b$ (III) Functionalized with Doxorubicin (DOX) Via PEG$_{5KDa}$-Valerate-Hydrazone (B-PEG$_{5KDa}$-VA-Hz-DOX) or PEG$_{5KDa}$-Carbonate-Hydrazone (B-PEG$_{5KDa}$-C-Hz-DOX) Linker The B-PEG$_{5KDa}$-VA-Hz-DOX and B-PEG$_{5KDa}$-C-Hz-DOX conjugates were obtained by mixing biotin-PEG$_{5KDa}$-VA-hydrazide or biotin-PEG$_{5KDa}$-C-hydrazide (example 1) in the presence of two equivalents of doxorubicin in anhydrous dimethylsulfoxide, acid for acetic acid. The hydrazones formation was followed by analyzing the reaction mixtures by means of gel filtration chromatography (Superdex peptide column, in Akta FPLC purifier-GE system). Upon completion of the reaction, the products were isolated by precipitation in ethyl ether, risolubilized in dichloromethane and reprecipitated in ether. The conjugated products identity (carbon 13 hydrazone of doxorubicin) was confirmed by $^1$H-NMR.

Nanoassembled (NP) consisting of avidin+pEGFp plasmid and α-biotin, ε-methoxy PEG$_{5KDa}$ (12.5% of the binding sites for biotin-BBS) were obtained and purified as indicated in example 2, and admixed with the B-PEG$_{5KDa}$-VA-Hz-DOX or B-PEG$_{5KDa}$-C-Hz-DOX derivative in the ratio of 0.5:1 to the biotin binding sites. After 1 hour, the mixtures were purified again by gel filtration. The number of DOX/NP molecules in the two assembled was calculated on the basis of the UV-Vis absorption spectrum of the product, taking into account the contribution of absorptivity at 480 nm and 280 nm of the doxorubicin and nanoparticles not loaded with the drug. The assembled products (ANANAS:B-PEG$_{5KDa}$-VA-Hz-DOX and ANANAS:B-PEG$_{5KDa}$-C-Hz-DOX) were found to contain about 530 and 400 molecules of doxorubicin/NP respectively.

Example 8. Synthesis of Nanoparticles with Biotinylated Compounds of Formula B—X$_a$-PA$_b$ (III) Functionalized with Doxorubicin Via PEG$_{5KDa}$-Valerate-Hydrazone (B-PEG$_{5KDa}$-VA-Hz-DOX) Linker, and of Formula B—X$_a$-PA$_b$ (II) Functionalized with Anti-Epidermal Growth Factor (EGFr) Antibody The anti EGFr antibody (cetuximab) has been conjugated with 2 biotin/IgG molecules by reaction with α-biotin, ω-N-hydroxysuccinimide PEG$_{5KDa}$ (Laysan bio) in phosphate buffer, pH 7.4. The biotin-PEG excess was removed by ultrafiltration (cut-off 30 kDa). The B-PEG$_{5KDa}$-VA-Hz-DOX conjugate was obtained as described in example 7. Nanoassembled products (NP) consisting of avidin+pEGFp plasmid and biotin-methoxy PEG-5 KDa were obtained as indicated in example 2. These were added to the biotinylated compound functionalized with the anti-EGFr antibody in a relationship IgG/NP=10/1. After 1 h, the mixture was added with B-PEG$_{5KDa}$-VA-Hz-DOX in a ratio of 0.5:1 with the biotin binding sites. After 1 hour, the mixture was purified by gel filtration. The number of DOX/NP molecules was calculated on the basis of the UV-Vis absorption spectrum of the product, taking into account the contribution of absorptivity at 480 nm and 280 nm of the different constituents of the system. The assembled (ANANAS:B-anti-EGFr:B-PEG$_{5KDa}$-VA-Hz-DOX) was found to contain 450 molecules of DOX/NP.

Example 9. Synthesis of Nanoparticles with Biotinylated Compounds of Formula B—X$_a$-PA$_b$ (III) Functionalized with Methyl-Prednisolone Via PEG$_{5KDa}$-Valerate-Hydrazone (PEG$_{5KDa}$-VA-Hz-MP) Linker The biotin-PEG-VA-hydrazo-methyl-prednisolone (B-PEG$_{5KDa}$VA-Hz-MP) conjugate was obtained by mixing biotin-PEG$_{5KDa}$-VA-hydrazide (example 1) in the presence of two equivalents of methyl-prednisolone (MP) in anhydrous dimethylsulfoxide acid for acetic acid. The formation of the hydrazone was followed by titrating the free hydrazide groups with the trinitrobenzene sulfonic (TNBS) reagent. When the reaction was complete, the product was isolated by precipitation in ethyl ether. The MP excess was removed by successive washes with ethyl ether, and the product dried under vacuum. The product identity (hydrazone at C3 of MP) was confirmed by $^1$H-NMR.

Nanoassembled products (NP) consisting of avidin+pEGFp plasmid and α-biotin, ε-methoxy PEG-PEG$_{5KDa}$ were obtained and purified as indicated in example 2. The nanoassembled was added with B-PEG$_{5KDa}$ VA-Hz-MP in a ratio of 1:1 with the binding sites for biotin. After 1 hour, the mixture was purified again by gel filtration. In order to titrate the number of MP/NP molecules, the assembled was treated with 0.1 M HCl for 3 h at 50° C. and the released MP was quantified by HPLC analysis (C18 column, water/acetonitrile/TFA eluents). The assembled (ANANAS:B-PEG$_{5KDa}$-VA-Hz-MP) was found to contain about 500 molecules of MP/NP.

Example 10. Release Kinetics of Dexamethasone from a) Nanoparticles with B—X$_a$-PA$_b$ Biotinylated Compounds Conjugated with PEG$_{5KDa}$-Carbonate-Hydrazone (PEG$_{5KDa}$C-Hz-DEX) Linker, b) Nanoparticles with PEG$_{5KDa}$-Valerate-Hydrazone (PEG$_{5KDa}$ VA-Hz-DEX) Linker and c) Nanoparticles with B—X$_a$-PA$_b$ Biotinylated Compounds Conjugated with PEG$_{5KDa}$-Carbonate-Hydrazone (PEG$_{5KDa}$ C-Hz-DEX)+B-Xa Biotinylated Compound with EZ-LC-Hydrazone Linker (EZ-LC-Hz-DEX)

Nanoparticles prepared according to example 2, example 3 and example 4, were placed in dialysis (cut-off 10 KDa) at 37° C. against 100 mM sodium phosphate buffer, pH 7.4 or 100 mM ammonium acetate buffer, pH 5.0 or 100 mM ammonium acetate buffer, pH 4.0. At predetermined times, the amount of dexamethasone released in acceptor solutions was quantified by HPLC (C18, CH$_3$CN/H$_2$O/TFA eluents). FIG. 3 shows the results obtained. The three nanoassembled products show release kinetics different depending on the type and degree of its hydrazone conjugated used in the assembly loading.

Example 11. Release Kinetics of Doxorubicin from Nanoparticles with B—X$_a$-PA$_b$ Biotinylated Compounds Conjugated with PEG$_{5KDa}$-Carbonate-Hydrazone (PEG$_{5KDa}$ C-Hz-DOX), and Nanoparticles with PEG$_{5KDa}$-Valerate-Hydrazone (PEG$_{5KDa}$ VA-Hz-Dox) Linker Nanoassembled products prepared according to example 7 were placed in dialysis at 37° C. against 100 mM sodium phosphate buffer, pH 7.4 or 100 mM sodium citrate buffer, pH 5.0, or 0.1M HCl. At predetermined times, the acceptor solutions and those in dialysis were analyzed by spectrofluorimetry or RP-HPLC (C18, CH$_3$CN/H$_2$O eluents) to quantify the doxorubicin released. FIG. 4 shows the release the results obtained, expressed in % of doxorubicin released in function of time (Mt) with respect to the total amount thereof present in the sample (Mtot). The two nanoassembled products release the drug with different kinetics, depending on the type of hydrazone conjugate used in the assembly.

Example 12. Release Kinetics of Triamcinolone from a) Nanoparticles with B—X$_a$-PA$_b$ Biotinylated Compounds Conjugated with PEG$_{5KDa}$-Carbonate-Hydrazone (PEG$_{3.4KDa}$C-Hz-TA) Linker, b) Nanoparticles with PEG$_{5KDa}$-Valerate-Hydrazone (PEG$_{5KDa}$ VA-Hz-TA) Linker Nanoparticles prepared according to examples 5, example 6, were placed in dialysis (cut-off 10 KDa) at 37° C. against 100 mM sodium phosphate buffer, pH 7.4 or 100 mM ammonium acetate buffer, pH 5.0 or 100 mM ammonium acetate buffer, pH 4.0. At predetermined times, the amount of triamcinolone acetonide released in acceptor solutions was quantified by HPLC (C18, CH$_3$CN/H$_2$O/TFA eluents). Table 1 summarizes the results obtained. The two nanoassembled products show release kinetics different depending on the type of hydrazone conjugated used in the assembly loading.

In the following Table 1 the results of release of the drugs conjugated by means of a hydrazone linkage to the nanoparticle of the nanoassembled complexes OF THE EXAMPLES are summarized (TA=triamcinolone acetonide; DEX=dexametasone; DOX=doxorubicin).

TABLE 1

| Drug [NP] | Examples | Drug/NP | pH of the release assay | Release % @72 h |
|---|---|---|---|---|
| TA [MW PEG = 3400; HZ derivative = SC BC = formula VIa] | 5, 12 | 790 | 7.4 | 0 |
| TA [MW PEG = 5000; HZ derivative = VA BC = formula Va] | 6, 12 | 670 | 7.4 | 9.3 |
| TA [MW PEG = 3400; HZ derivative = SC BC = formula VIa] | 5, 12 | 790 | 5.0 | 0 |
| TA [MW PEG = 5000; HZ derivative = VA BC = formula Va] | 6, 12 | 670 | 5.0 | 15.3 |
| TA [MW PEG = 3400; HZ derivative = SC BC = formula VIa] | 5, 12 | 790 | 4.0 | 13.2 |
| TA [MW PEG = 5000; HZ derivative = VA BC = formula Va] | 6, 12 | 670 | 4.0 | 37.2 |
| DEX [MW PEG = 5000; HZ derivative = SC BC = formula VIa] | 3, 10 | 530 | 7.4 | 0 |
| DEX [MW PEG = 5000; HZ derivative = VA BC = formula Va] | 2, 10 | 522 | 7.4 | 0 |
| DEX [MW PEG = 5000 + 0 No PEG linker; HZ derivative = SC + LC; BC = formula VIa + XIa] | 4, 10 | 850 (530 + 320) | 7.4 | 0 |
| DEX [MW PEG = 5000; HZ derivative = SC BC = formula VIa] | 3, 10 | 530 | 5.0 | 1.9 |
| DEX [MW PEG = 5000; HZ derivative = VA BC = formula Va] | 2, 10 | 522 | 5.0 | 1.2 |
| DEX [MW PEG = 5000 + 0 No PEG linker; HZ derivative = SC + LC; BC = formula VIa + XIa] | 4, 10 | 850 (530 + 320) | 5.0 | 1.4 |
| DEX [MW PEG = 5000; HZ derivative = SC BC = formula VIa] | 3, 10 | 530 | 4.0 | 15.4 |
| DEX [MW PEG = 5000; HZ derivative = VA BC = formula Va] | 2, 10 | 522 | 4.0 | 28.4 |
| DEX [MW PEG = 5000 + 0 No PEG linker; HZ derivative = SC + LC; BC = formula VIa + XIa] | 4, 10 | 850 (530 + 320) | 4.0 | 10.6 |

| Drug [NP] | Examples | Drug/NP | pH of the release assay | Release % @17 h |
|---|---|---|---|---|
| DOX [MW PEG = 5000: HZ derivative = SC BC = formula VIa] | 7, 11 | 400 | 7.4 | 41.5 |
| DOX [MW PEG = 5000; HZ derivative = VA | 7, 11 | 530 | 7.4 | 0 |

TABLE 1-continued

| | | | | |
|---|---|---|---|---|
| DOX [MW PEG = 5000; HZ derivative = SC BC = formula Va] | 7, 11 | 400 | 5.0 | 46.3 |
| DOX [MW PEG = 5000; HZ derivative = SC BC = formula VIa] | 7, 11 | 530 | 5.0 | 6 |
| DOX [MW PEG = 5000; HZ derivative = VA BC = formula Va] | 7, 11 | 400 | 1.0 | 90 |
| DOX [MW PEG = 5000; HZ derivative = SC BC = formula VIa] | 7, 11 | 530 | 1.0 | 80 |
| DOX [MW PEG = 5000; HZ derivative = VA BC = formula Va] | | | | |

REFERENCES

Wilchek M and Bayer E A, *Analytical Biochemistry* 1988, 171, 1-32.

Wilchek M and Bayer E A, *Methods Enzymol.* 1990, 184, 14-45.

Goldenberg D M, Sharkey R M, Paganelli G, Barbet J, and Chatal J F, *J. Clin. Oncol.* 2006, 24: 823-834.

Morpurgo M, Radu A, Bayer E A, and Wilchek M, *J. Mol. Rec.* 2004, 17, 558-566.

Morpurgo M, Pignatto M, Teoli D, WO 2009/003951.

Pignatto M, Realdon N, Morpurgo M, *Bioconjugate Chem.*, 2010, 21, 1254-1263.

Morpurgo M, Facchin S, Pignatto M, Silvestri D, Casarin E, Realdon N, *Analytical Chemistry*, 2012, 84, 3433-3439.

Bigini P, Previdi S., Casarin E, Silvestri D, Violatto M B, Facchin S, Sitia L, Rosato, Zuccolotto G, Realdon N, Fiordaliso F, Salmona M and Morpurgo M. *ACS Nano American Chemical Society*, 2014, 8, 175-187.

Owens D E and Peppas N A, *Int. J. Pharm.* 2006, 307: 93-102.

The invention claimed is:

1. Nanoassembled complexes comprising a nucleus consisting of an oligonucleotide sequence and one or more avidin units auto-assembled by means of high-affinity interactions between avidin and one or more nucleobases of the oligonucleotide sequence, and biotinylated compounds assembled on biotin binding sites on the avidin of the nucleus by high-affinity interactions between avidin and biotin, the complexes having the general formula (I)

$$NB_n Av_y (BC)_z \quad (I)$$

wherein:

NB is a nucleobase of the oligonucleotide sequence of a single or double stranded nucleic acid and n is a number higher than 16 and up to 100,000;

Av is a tetrameric avidin unit and y is an integer higher than or equal to 1 and is in relation to n in a range from $(0.0001) \cdot n$ to $(0.0454) \cdot n$ with the proviso that if $(0.0001$ to $0.045) \cdot n$ is less than 1, y is equal to 1;

BC is a biotinylated compound and z is an integer higher than or equal to 1 and is in relation to y in a range from $(0.02) \cdot y$ to $(4) \cdot y$ with the proviso that if $(0.02$ to $4) \cdot y$ is less than 1, z is equal to 1;

wherein at least 5% of the BC of Formula I is formula B-Xa-PAb (III), wherein B is a biotin residue, X is a linker having at least two functionalizable residues, PA is a polymeric unit of a hydrophilic polymer having at least two functionalizable residues, wherein the first functionalizable residue of the PA binds the biotin residue B with a covalent bond either directly or through the linker X by means of a carboxylic functional group thereof and the second functionalizable residue of the PA consists of a hydrazine residue selected from the group consisting of —R—C(=O)—NHNH$_2$, —R—O—C(=O)—NHNH$_2$, —R—NH—(C=O)—NHNH$_2$, —R—NH—(C=S)—NHNH$_2$, and —R—(C$_6$H$_4$)—NHNH$_2$ where R is a linear or branched C$_1$-C$_{10}$ alkyl residue, a is a number from 0 to 10, and b is a number from 1 to 20;

wherein the remaining BC of Formula I is selected from compounds:

(i) B—X$_a$-PA$_b$ (II) wherein B is a biotin residue, X is a linker having at least two functionalizable residues, PA is a polymeric unit of a hydrophilic polymer having at least two functionalizable residues, wherein the first functionalizable residue of the polymeric unit binds the biotin residue B with a covalent bond either directly or through the linker X by means of a carboxylic functional group thereof and the second functionalizable residue of the polymeric unit is free, is protected with protective groups, or binds fluorophores or targeting molecules, a is a number from 0 to 10, and b is a number from 1 to 20; or (ii) B—X$_a$ (IV) wherein B is a biotin residue, X is a linker having at least two functionalizable residues, wherein the first functionalizable residue of X binds the biotin residue B with a covalent bond directly by means of a carboxylic functional group thereof and the second functionalizable residue of X is a hydrazine residue selected from the group consisting of

—R—C(=O)—NHNH$_2$, —R—O—C(=O)—NHNH$_2$,

—R—NH—(C=O)—NHNH$_2$,

—R—NH—(C=S)—NHNH$_2$, and —R—(C$_6$H$_4$)—NH—NH$_2$ where R is a linear or branched C$_1$-C$_{10}$ alkyl residue, a is a number in the range of from 1 to 10, wherein the biotinylated compounds of formula (III) and/or (IV) are reversibly conjugated to bioactive molecules having at least one carbonyl group via the hydrazine residue.

2. The nanoassembled complexes according to claim 1, wherein n is in the range of 30 to 50,000.

3. The nanoassembled complexes according to claim 2, wherein n is in the range of 3,000 to 20,000.

4. The nanoassembled complexes according to claim 1, wherein y is in the range of (0.01)•n to (0.0454)•n.

5. The nanoassembled complexes according to claim 1, wherein z is in the range of (0.4)•y to (4)•y.

6. The nanoassembled complexes according to claim 1, wherein a of formula (II) or (III) is a number from 0 to 5 and a of formula (IV) is a number from 1 to 5.

7. The nanoassembled complexes according to claim 1, wherein b of formula (II) or (III) is a number from 1 to 10.

8. The nanoassembled complexes according to claim 1, wherein the polymeric unit PA is selected from the group consisting of polyethylene glycol and a copolymer of polyethylene glycol and polyoxypropylene.

9. The nanoassembled complexes according to claim 1, wherein the polymeric unit PA has a molecular weight of from 400 to 20,000.

10. The nanoassembled complexes according to claim 9, wherein the polymeric unit PA has a molecular weight of from 1,000 to 5,000.

11. The nanoassembled complexes according to claim 1, wherein the linker X of formula (II) and of formula (III) is a bifunctional compound according to the general formula (XV)

Y—R$^1$—Y'  (XV)

Wherein Y and Y' are equal to or different from each other, and are selected from the group consisting of —COO—, —NH—, —O—, —SO$_2$—, —S—, —SO—, —CO—, —COS—, —NH—CO—, —NH—COO—, and —HN—SO—NH—; and R$^1$ is selected from the group consisting of alkyl, alkenyl, alkynyl, cycloalkyl and aryl, with a carbon atom number of from 1 to 20, optionally substituted.

12. The nanoassembled complexes according to claim 1, wherein the linker X of formula (II) and of formula (III) is a polyfunctional linker and has at least 3 functional groups.

13. The nanoassembled complexes according to claim 12, wherein the polyfunctional linker is selected from the group consisting of lysine, glutamic acid, aspartic acid, cysteine, and a dendrimer.

14. The nanoassembled complexes according to claim 12, wherein the polyfunctional linker is lysine.

15. The nanoassembled complex according to claim 1, wherein the hydrazine residue for the biotinylated compounds of formula (III) and (IV) is selected from —R—C(=O)—NHNH$_2$, or —R—O—C(=O)—NHNH$_2$.

16. The nanoassembled complex according to claim 1, wherein the bioactive molecules are selected from steroidal or non-steroidal anti-inflammatory, anticancer, antibiotic or anti-gout agents.

17. The nanoassembled complex according to claim 16, wherein the steroidal anti-inflammatory agents are selected from hydrocortisone, dexamethasone, triamcinolone, triamcinolone acetonide or hexaacetonide, prednisolone or methylprednisolone.

18. The nanoassembled complex according to claim 16, wherein the non-steroidal anti-inflammatory agents are selected from droxicam, tenoxicam, ketoprofen, tolmentine, nabumetone or ketorolac.

19. The nanoassembled complex according to claim 16, wherein the anticancer agents are selected from doxorubicin, daunomycin, epirubicin, idarubicin, paclitaxel, docetaxel, cabazitaxel, or cyproterone.

20. The nanoassembled complex according to claim 16, wherein the antibiotic agents are selected from doxycycline, chlortetracycline, erythromycin, oleandomycin, clarithromycin, or flurithromycin.

21. The nanoassembled complex according to claim 16, wherein the anti-gout agent is colchicine.

22. A method for the therapeutic treatment of a disease selected from inflammatory pathologies, cancer, infections and or gout comprising: administrating to a patient in need thereof a therapeutically effective amount of the nanoassembled complexes according to claim 1.

23. The method according to claim 22, wherein the inflammatory pathologies are selected from acute, chronic osteoarticular pathologies, or autoimmune pathologies.

24. A drug conjugate of nanoassembled complexes according to claim 1.

25. A method for the therapeutic treatment of a disease selected from inflammatory pathologies, cancer, infections or gout comprising: administrating to a patient in need thereof a therapeutically effective amount of the drug conjugate of nanoassembled complex according to claim 24.

26. The method according to claim 25, wherein the inflammatory pathologies are selected from acute, chronic osteoarticular pathologies, or autoimmune pathologies.

* * * * *